United States Patent [19]

Putter et al.

[11] Patent Number: 4,678,774

[45] Date of Patent: Jul. 7, 1987

[54] NOVEL SYNERGISTIC COMPOSITIONS

[75] Inventors: Irving Putter, Martinsville, N.J.; Daniel M. Stout, Kirkwood, Mo.

[73] Assignee: Merck & Co., Inc., Rahway, N.J.

[21] Appl. No.: 741,926

[22] Filed: Jun. 6, 1985

[51] Int. Cl.[4] .................. A01N 43/04; A01N 25/00
[52] U.S. Cl. ................................ 514/30; 514/770
[58] Field of Search .................... 514/30, 770

[56] References Cited

U.S. PATENT DOCUMENTS

| | | | |
|---|---|---|---|
| 4,001,379 | 1/1977 | Türk et al. | 514/770 |
| 4,141,971 | 2/1979 | Krausz et al. | 514/30 |
| 4,171,314 | 10/1979 | Chabala et al. | 536/7.1 |
| 4,173,571 | 11/1979 | Chabala et al. | 536/7.1 |
| 4,199,569 | 4/1980 | Chabala et al. | 514/30 |
| 4,304,769 | 12/1981 | Chen | 424/78 |
| 4,310,519 | 1/1982 | Albers-Schonberg et al. | 514/30 |
| 4,427,663 | 1/1984 | Mrozik | 514/30 |
| 4,469,682 | 9/1984 | Mrozik | 536/7.1 |

OTHER PUBLICATIONS

Fisher et al., "The Avermectin Family of Macrolide–Like Antibiotics", chapter 14, pp. 553–606, Macrolide Antibiotics, Chemistry, Biology and Practice, Academic Press (1984).
"Cab–O–Sil Properties and Function", p. 6.
"Bio–Rad Price List L January 1986", pp. 30–31.
Tarshin, *Pest Control*, Jun. 1959, pp. 14, 16–18, 20, 22, 24 and 26–28.
Arthur et al., *Journal of Economic Entomology* 66, 907–908 (1973).
Moore, *Journal of Economic Entomology* 65, 458–461, (1972).
*Chemical Week*, Aug. 1, 1984, p. 35.
Urba et al., *Canadian Journal of Zoology*, 61, pp. 1481–1486, (1983).

*Primary Examiner*—Albert T. Meyers
*Assistant Examiner*—John M. Kilcoyne
*Attorney, Agent, or Firm*—David L. Rose; Michael C. Sudol, Jr.

[57] ABSTRACT

There are disclosed novel formulations of avermectin compounds and a substrate which demonstrate markedly enhanced insecticidal activity over that which would be observed with other formulations. Avermectin natural product compounds and certain semisynthetic derivatives thereof are compounds known to be highly effective broad-spectrum antiparasitic and pesticidal agents. However, when such compounds are formulated into the instant composition, the activity observed is increased to at least 10-times that which would be expected. The instant substrate is preferably a highly dispersed, amorphous form of hydrophyllic silicon dioxide.

4 Claims, No Drawings

NOVEL SYNERGISTIC COMPOSITIONS

BACKGROUND OF THE INVENTION

Avermectin compounds are a series of natural products isolated from the fermentation broth of a strain of *Streptomyces avermitilis*. The series consists of eight compounds, 4 major and 4 minor. The compounds are disclosed in U.S. Pat. No. 4,310,519. Certain derivatives of such compounds are also disclosed such as the 22,23-dihydro derivatives described in U.S. Pat. No. 4,199,569. The 13-deoxy derivatives of avermectin compounds are disclosed in U.S. Pat. Nos. 4,171,314 and 4,173,571. Avermectins with a 4''-amino group are also highly efficaceous in this invention and are disclosed in U.S. Pat. No. 4,427,663. In addition, the 4''-phosphate derivatives of the avermectin compounds with a 13-O-disaccharide group present are included in the instant combination. Such compounds are disclosed in copending U.S. Pat. application Ser. No. 461,843, now U.S. Pat. No. 4,469,682.

SUMMARY OF THE INVENTION

The instant disclosure describes certain synergistic compositions of avermectin compounds and highly dispersed hydrophyllic amorphous silicon dioxide which have considerable activity against insects. Thus, it is an object of this invention to describe such synergistic compositions. It is a further object to describe the process used to prepare such synergistic compositions. A still further object is to describe the insecticidal effects of such compositions. Further objects will become apparent from a reading of the following description.

DESCRIPTION OF THE INVENTION

The instant invention consists of a composition of avermectin compounds and a substrate which has an activity against insects of at least 10 times what will be expected from other avermectin compositions.

Avermectin compounds of this invention have the following structure:

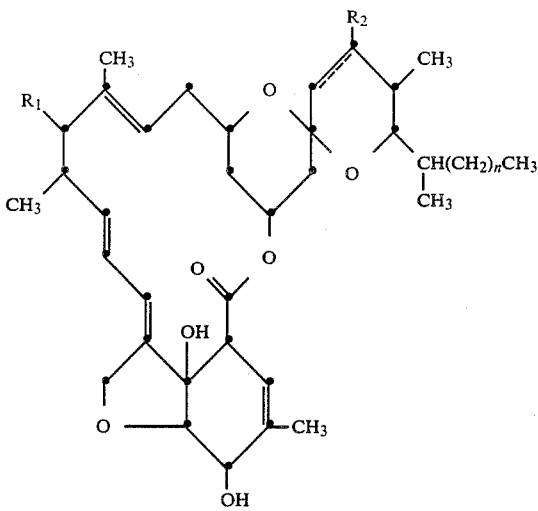

wherein
n is 0 or 1;
$R_1$ is hydrogen, α-L-oleandrosyl-α-L-oleandrosyloxy and the 4''-phosphate and 4''-amino derivatives thereof;
$R_2$ is hydrogen or hydroxy; and
the broken line indicates a single or a double bond; however, $R_2$ is present only when the broken line indicates a single bond.

The highly dispersed, hydrophyllic amorphous silicon dioxide which is useful in this invention is available from various manufacturers such as the various forms of Aerosil ® available from Degussa Corporation. The highly dispersed, amorphous silicon dioxide is of a high surface area ranging from 35 to over 400 m² per gram and an average primary particle size of about 7 to 40 nanometers, and a standard, uncompressed density of about 40 to 130 g/l. In addition, appropriate forms of silicon dioxide are available as various forms of Cab-O-Sil available from the Cabot Corporation.

The hydrophyllic characterization of the silicon dioxide is determined by the extent of silanol groups present. A particular form of silicon dioxide will be hydrophyllic if it has a preponderance of unreacted silanol groups such that the carbon content is well under 1% (a carbon content of 1% will characterize an amorphous silicon dioxide as hydrophobic).

The instant formulation is prepared by dissolving the avermectin compound in any organic solvent in which the compound is soluble such as acetone, methylene chloride, ether, tetrahydrofuran, and the like and suspending therein the highly dispersed, hydrophyllic amorphous silicon dioxide which is insoluble in the organic solvent. The solvent is then removed completely forming the instant dry-powdered formulation of the avermectin on the substrate. When this procedure is followed, the avermectin is very tightly bound to the substrate and, in fact, is so highly bound that subsequent solvent washes, even with the same solvent used to prepare the formulation initially, will not remove the avermectin from the substrate. This is an advantage when the instant dry-powdered formulation is utilized with other adjuvants, in particular liquid adjuvants for further formulation that will not remove the avermectin from the substrate.

In the instant formulation, the avermectin and the highly dispersed, amorphous silicon dioxide are present in a ratio of from $10^{-3}$ to $10^2$ on the basis of μg of the avermectin per mg of the silicon dioxide, preferably at a ratio of about $10^{-2}$ to 10 μg/mg.

When used as an insecticidal agent, the instant synergistic composition containing from 10 to $10^4$ ppm of the avermectin compound is applied at dosage rates of from 0.01 to 100 mg of the composition per square meter of the surface to be treated.

The synergistic effects of the instant composition of the avermectin compounds with the substrate are observed in providing for a reduced dosage of the avermectin compound. Thus, a lessened quantity of the insecticidal compound is applied than normally would be required, which results in a lessening of possible side-effects and a lessening in the development of resistance. Thus, the instant composition provides for a formulation which will eliminate insect pests much more economically than would be anticipated from the avermectin compound alone. In addition the stability of the avermectin compounds has been seen to be increased by using the instant formulation.

The insect pests against which the instant synergistic composition is effective are termites, roaches, ants, leafminers and other domestic and agricultural insect pests.

A further aspect of this invention is that the instant formulation may be modified by substituting other insecticidal agents for the above avermectin compounds. Certain other insecticidally active compounds have been found to be sufficiently tightly bound to the substrate such as boric anhydride, chlorpyriphos, propoxur and pyrethrin. Such insecticidal agents are formulated with the substrate in the same manner as are the avermectins, using a solvent suitable for the insecticidal agent.

The instant synergistic composition is applied most conveniently as a part of a spray, bait, or powder formulation. The spray formulation may be aqueous or non-aqueous with the composition dissolved or suspended therein. As noted above, the very tight binding of the avermectin compound to the substrate will allow for the use of liquid formulations since the avermectin compound will not be dissolved from, or otherwise removed from the silicon dioxide substrate. Emulsifiers, suspending agents and other formulation adjuvants may be included in the formulation as required. Any liquid suspension formulation commonly used by those familiar with the technique of insecticidal spray formulations may be employed. Hand-held, hand-powered or electric-powered sprays as well as aerosols are suitable for household uses while gasoline-powered or aerial applications are generally used for larger scale and commercial applications. Such spray techniques are suitable for those applications where direct application to the insect pest's feeding area or habitat are desired. When used against termites, those skilled in the art will appreciate that the instant composition may be applied either in a liquid suspension or dry powder into the ground to form the insecticidal barrier between the termite's nest in the soil and the area to be protected by termite infestation.

Another formulation suitable for such direct application is a powder formulation which may be dusted into those areas where the insect pest feeds, traverses or lives. The instant dry synergistic composition may be combined with other dry ingredients using techniques known to those skilled in the art.

The instant synergistic composition may be formulated as a bait which has the advantage that the insects which mostly remain in the nest and those insects which have nests that are difficult to locate are treated. Bait formulations are particularly advantageous with respect to the avermectin compound considering its long duration of activitiy and high potency which is even further potentiated by the instant synergistic composition.

The bait formulations are prepared from animal or vegetable material which serves as food for the insect pests. Sugar solutions used in the liquid form or added to other materials are particularly useful. The addition of the synergistic combination to meat products such as prepared pet foods, results in a very useful bait formulation. The synergistic formulation may also be combined as a suspension or solution in a vegetable oil such as soybean oil, sesame oil, cottonseed oil, and the like, and combined with a dry vegetable matter such as defatted corn grits, citrus pulp, sugarcane pulp and the like and molded into bait formulations of any size or shape.

In addition to the primary ingredients, the bait formulation may contain other ingredients such as stabilizers, suspending agents, emulsifiers, and the like.

The synergistic effects of the instant formulation are realized when avermectin Bla and Blb in an approximately 80:20 mixture is combined with silicon dioxide according to the above-described process and tested against termites (avermectin Bla is realized in the above structural formula when the dotted line indicates a double bond $R_1$ is $\alpha$-L-oleandrosyl-$\alpha$-L-oleandrosyloxy, $R_2$ is not present and n is 1 and avermectin Blb is the analagous compound where n is zero). The data are shown in Table I which indicates that highly dispersed, hydrophilic amorphous silicon dioxide alone has no effect on the termites and that avermectin Bla and Blb alone has limited effects only at quantities of 1 microgram and higher but that the combination has substantialy greater effects. For example, 0.01 micrograms of avermectin has an $LT_{50}$ and $LT_{100}$ (lethal times for 50 and 100% mortality respectively of the test insects to be killed) in excess of 14 days while the same 0.01 micrograms of avermectin on 1 milligram of silicon dioxide has an $LT_{50}$ of 3 days and an $LT_{100}$ of 6 days. Similar results are observed at the other dosages shown.

TABLE I

Activity of Avermectin Bla/Blb Against Termites

| Sample* | $LT_{50}$ (days) | $LT_{100}$ (days) |
|---|---|---|
| Silicon Dioxide - 1.0 | >14 | >14 |
| Silicon Dioxide - 10.0 | >14 | >14 |
| Silicon Dioxide - 100.0 | >14 | >14 |
| Avermectin Bla/Blb - 0.01 | >14 | >14 |
| Avermectin Bla/Blb - 0.01 + Silicon Dioxide - 1.0 | 3 | 6 |
| Avermectin Bla/Blb - 0.01 + Silicon Dioxide - 10.0 | 3 | 10 |
| Avermectin Bla/Blb - 0.1 | >14 | >14 |
| Avermectin Bla/Blb - 0.1 + Silicon Dioxide - 1.0 | 2.5 | 4 |
| Avermectin Bla/Blb - 0.1 + Silicon Dioxide - 10.0 | 3 | 4 |
| Avermectin Bla/Blb - 1.0 | 2.5 | 7 |
| Avermectin Bla/Blb - 1.0 + Silicon Dioxide - 1.0 | 1 | 3 |
| Avermectin Bla/Blb - 1.0 + Silicon Dioxide - 10.0 | 1 | 2 |
| Avermectin Bla/Blb - 10.0 | 1.5 | 3 |
| Avermectin Bla/Blb - 10.0 + Silicon Dioxide - 1.0 | 1 | 1 |
| Avermectin Bla/Blb - 10.0 + Silicon Dioxide - 10.0 | 1 | 1.5 |

*All Silicon Dioxide samples in milligrams of Cab-O-Sil M5
All Avermectin samples in micrograms Additionally Table II demonstrates the synergism, and Tables III and IV demonstrate the efficacy of the avermectin on highly dispersed amorphous silicon dioxide against the termite *R. Flavipes*. In this assay the avermectin and the silicon dioxide were applied singly or in combination to glass petri dishes. After swirling the solution of suspension, the solvent was evaporated and the residue remained as a uniform deposit on the floor of the dish. A small water moistened paper block (about 0.3×2.5×2.5 cm) was set in the center of the dish as a source of food and moisture for the termites. After 20 worker termites were placed in the dish, inspections were made daily for 14 days. At inspection, any dead termites were removed and counted and the pulp block remoistened as needed.

TABLE II

Number of dead R. flavipes with time in three replicate exposures of 20 workers to Avermectin B, and two carriers in a petri dish assay

| Deposits in dish | | Mortality | |
|---|---|---|---|
| Avermectin μg | SiO₂ Cab O Sil M5 mg | Average number of dead at 14 days | Time to complete mortality + SD (days) |
| 10 | — | 20.0 | 4.0 ± 0.0 |
| 1 | — | 20.0 | 7.3 ± 0.5 |
| 0.1 | — | 7.3 | >14.0 |
| 0.01 | — | 0.3 | >14.0 |
| — | 100 | 0.3 | >14.0 |
| — | 10 | 2.0 | >14.0 |
| — | 1 | 2.0 | >14.0 |
| — | 0.1 | — | — |
| 10 | 1 | 20.0 | 1.0 ± 0.0 |
| 1 | 1 | 20.0 | 3.3 ± 1.2 |
| 0.1 | 1 | 20.0 | 4.3 ± 0.6 |
| 0.01 | 1 | 20.0 | 6.7 ± 1.2 |
| 10 | 10 | 20.0 | 2.0 ± 0.0 |
| 1 | 10 | 20.0 | 3.3 ± 1.2 |
| 0.1 | 10 | 20.0 | 4.3 ± 0.6 |
| 0.01 | 10 | 20.0 | 9.3 ± 2.9 |
| 0 | 0 | 0.0 | >14.0 |

TABLE III

Time for complete mortality of R. flavipes during three replicate exposures each with 20 termites, with various Avermectin B, to Cab O Sil M5 ratios and a constant 0.1 mg of avermectin/bioassay dish

| Deposit in dish | | Time to complete mortality |
|---|---|---|
| Avermectin μg | Dust mg | x̄ + SD days |
| 0.1 | 0.001 | 9.7 + 3.1 |
| 0.1 | 0.01 | 3.7 + 1.5 |
| 0.1 | 0.1 | 1.7 + 0.6 |
| 0.1 | 1.0 | 2.7 + 0.6 |
| 0.1 | 10.0 | 2.0 + 0.0 |

A specific example for the preparation of the instant synergistic composition is as follows, however, such example should not be considered as limitative of the invention:

In 5 ml of acetone is dissolved in 0.5 mg of avermectin Bla and Blb present in a ratio of approximately 80:20. When dissolution is complete 100 mg of Cab-O-Sil M5 (available from Cabot Corporation) is added and the suspension stirred for 5 minutes at room temperature. The suspension is evaporated to dryness in vacuo affording a dry powder which contained 0.05 μg/mg of the avermectins on the highly dispersed, hydrophyllic amorphous silicon dioxide.

What is claimed is:

1. An insecticidal synergistic composition consisting of an avermectin compound having the formula:

wherein
n is 0 or 1; and
$R_1$ is α-L-oleandrosyl-α-L-oleandrosyloxy;
absorbed onto highly dispersed, hydrophyllic amorphous silicon dioxide which has a surface area of from 35 to 400 m² per gram, an average particle size of from 7 to 40 nanometers and a standard uncompressed density of about 40 to 130 g/l and wherein the avermectin compound is present on the silicon dioxide at a ratio of from $10^{-3}$ to $10^2$ μg of the avermectin per mg of the silicon dioxide.

2. The insecticidal composition of claim 1 wherein the avermectin compound is present on the silicon dioxide at a ratio of about $10^{-2}$ to 10 μg of the avermectin per mg of the silicon dioxide.

3. A process for the preparation of the synergistic composition of claim 1 which comprises dissolving the avermectin compound in sufficient organic solvent in which the compound is soluble, selected from acetone, methylene chloride, ether or tetrahydrofuran; combining the resultant solution with the silicon dioxide; and completely evaporating the solvent from the resultant suspension.

4. The process of claim 3 wherein the solvent is acetone.

* * * * *